United States Patent
Kareis

(10) Patent No.: US 10,512,270 B2
(45) Date of Patent: Dec. 24, 2019

(54) ACID TABLET COMPOSITION AND METHODS OF PREPARING AND USING THE SAME

(71) Applicant: Axiall Ohio, Inc., Atlanta, GA (US)

(72) Inventor: Christopher M. Kareis, Monroeville, PA (US)

(73) Assignee: Eagle US 2 LLC, Houston, TX (US)

( * ) Notice: Subject to any disclaimer, the term of this patent is extended or adjusted under 35 U.S.C. 154(b) by 30 days.

(21) Appl. No.: 15/469,998

(22) Filed: Mar. 27, 2017

(65) Prior Publication Data

US 2017/0280727 A1    Oct. 5, 2017

Related U.S. Application Data

(60) Provisional application No. 62/317,245, filed on Apr. 1, 2016.

(51) Int. Cl.
| | |
|---|---|
| *A01N 59/02* | (2006.01) |
| *A01N 25/34* | (2006.01) |
| *A01N 37/02* | (2006.01) |
| *A23B 7/10* | (2006.01) |
| *A61L 2/18* | (2006.01) |
| *C02F 1/00* | (2006.01) |
| *C02F 1/66* | (2006.01) |
| *C02F 1/68* | (2006.01) |
| *C02F 103/02* | (2006.01) |

(52) U.S. Cl.
CPC ............. *A01N 59/02* (2013.01); *A01N 25/34* (2013.01); *A01N 37/02* (2013.01); *A23B 7/10* (2013.01); *A61L 2/18* (2013.01); *C02F 1/008* (2013.01); *C02F 1/66* (2013.01); *C02F 1/68* (2013.01); *A23V 2002/00* (2013.01); *C02F 2103/02* (2013.01); *C02F 2209/06* (2013.01); *C02F 2303/04* (2013.01)

(58) Field of Classification Search
None
See application file for complete search history.

(56) References Cited

U.S. PATENT DOCUMENTS

| | | | |
|---|---|---|---|
| 3,276,949 A | 10/1966 | Robson et al. | |
| 4,192,763 A | 3/1980 | Buchan | |
| 4,666,610 A | 5/1987 | Kuhns | |
| 6,432,322 B1 | 8/2002 | Speronello et al. | |
| 6,602,442 B1 | 8/2003 | Pitochelli | |
| 6,699,404 B2 | 3/2004 | Speronello et al. | |
| 6,982,097 B2 | 1/2006 | Mingzhong et al. | |
| 7,048,803 B2 | 5/2006 | Williams | |
| 7,090,882 B2 | 8/2006 | Koefod et al. | |
| 7,150,854 B2 | 12/2006 | Koermer et al. | |
| 7,182,883 B2 | 2/2007 | Speronello et al. | |
| 7,682,513 B2 | 3/2010 | Wang | |
| 7,820,198 B2 | 10/2010 | Blanchette et al. | |
| 8,147,673 B2 | 4/2012 | Childers, II et al. | |
| 8,318,231 B2 | 11/2012 | Warf, Jr. et al. | |
| 8,372,291 B2 | 2/2013 | Mullins et al. | |
| 8,496,817 B2 | 7/2013 | Just | |
| 2004/0046149 A1 | 3/2004 | Meyer | |
| 2005/0139805 A1 | 6/2005 | Koster | |
| 2005/0266097 A1 | 12/2005 | Meyer | |
| 2006/0102874 A1 | 5/2006 | Zheng | |
| 2006/0110453 A1 | 5/2006 | Brennan et al. | |
| 2010/0072144 A1 | 3/2010 | Osakabe et al. | |
| 2010/0112595 A1 | 5/2010 | Liu et al. | |
| 2011/0309297 A1 | 12/2011 | Thangaraj et al. | |
| 2013/0020265 A1 | 1/2013 | Kamatsuchi et al. | |
| 2014/0308371 A1 | 10/2014 | Parasida et al. | |

FOREIGN PATENT DOCUMENTS

| | | |
|---|---|---|
| CN | 102687728 A | 9/2012 |
| CN | 104995133 A | 10/2015 |
| WO | 0134524 A1 | 5/2001 |
| WO | 2004093847 A1 | 11/2004 |
| WO | 2007024340 A2 | 3/2007 |
| WO | 2008041470 A1 | 4/2008 |
| WO | 2011062202 A1 | 5/2011 |
| WO | 2014157484 A1 | 10/2014 |

OTHER PUBLICATIONS

Liu et al.; "Chlorination of bromide-containing waters: Enhanced bromate formation in the presence of synthetic metal oxides and deposits formed in drinking water distribution systems"; Water Research; 2013; pp. 5307-5315; vol. 47.

*Primary Examiner* — Jessica Worsham
(74) *Attorney, Agent, or Firm* — The Webb Law Firm

(57) ABSTRACT

Compositions, tablets, prills and granules are provided including (a) about 95 to about 99.999 weight percent of at least one alkali metal hydrogen sulfate; and (b) about 0.001 to less than 0.08 weight percent of at least one alkali metal salt of a fatty carboxylic acid and/or at least one alkaline earth metal salt of a fatty carboxylic acid; wherein the composition includes less than 1 weight percent of chlorite and/or hypochlorite and less than 1 weight percent of alkali metal salt and/or alkaline earth metal salt that is chemically different from the at least one alkali metal hydrogen sulfate, the at least one alkali metal salt of a fatty carboxylic acid and the at least one alkaline earth metal salt of a fatty carboxylic acid, on a basis of total weight of the composition. Methods of use also are provided.

37 Claims, 3 Drawing Sheets

ACID TABLET COMPOSITION AND METHODS OF PREPARING AND USING THE SAME

CROSS-REFERENCE TO RELATED APPLICATION

The present application claims priority from U.S. Provisional Patent Application No. 62/317,245, filed on Apr. 1, 2016, which is incorporated herein by reference in its entirety.

FIELD OF THE INVENTION

The present invention relates to a composition, tablet, prill or granule that comprises at least one alkali metal hydrogen sulfate and about 0.001 to less than 0.08 weight percent of at least one alkali metal salt of a fatty carboxylic acid and/or at least one alkaline earth metal salt of a fatty carboxylic acid on a basis of total weight of the composition, and to methods of making the same and treating an aqueous stream with such compositions, tablets, prills or granules. Also provided is an acidification tablet for acidifying an aqueous solution consisting of at least one alkali metal hydrogen sulfate and methods of making the same and treating an aqueous stream with the same.

BACKGROUND OF THE INVENTION

Modifying the pH of a water source, such as a water source that includes a source of free available halogen, can be desirable in certain applications, such as the cleaning and/or sanitizing of food and/or equipment surfaces by application of the water source thereto. In some applications it is desirable to reduce the pH of the water source, such as to less than 7. Reducing the pH of a water source can serve to reduce the alkalinity of the water, such as alkalinity due to aqueous bicarbonate, which if not reduced can result in the undesirable formation of scale, such as calcium carbonate scale, on surfaces that come into contact with the water. Reducing the pH of a water source that includes free available halogen, such as free available chlorine, can serve to desirably enhance the sanitizing properties of the free available halogen and correspondingly reduce or minimize the occurrence of undesirable microbes, such as bacteria, yeasts, and/or molds, within the water source itself and/or on surfaces to which it is applied. In some applications, it is desirable to controllably modify the pH of the water source, such that it has a pH value residing within a predetermined range. If the pH of the water source is outside of the predetermined range, the cleansing and/or sanitizing properties of the water source may be undesirably reduced.

With some applications, the pH of a water source can be reduced by the addition of a liquid acid, such as hydrochloric acid (HCl) or aqueous solutions of citric acid, thereto. Controllably introducing a liquid acid to the water source can be difficult in some instances, resulting in pH values that reside outside of a predetermined range. In addition, storage of the liquid acid can raise issues relating to safety and environmental impact, and related increased costs, such as increased costs associated with providing secondary containment of the liquid acid if storage containers containing the liquid acid are breached. Handling of the liquid acid (e.g., HCl) can raise safety and corrosion issues, such as exposure of workers and equipment to the liquid acid or its vapors.

It would be desirable to develop new compositions and methods that can be used to modify the pH of a water source. It would be further desirable that such newly developed compositions and methods provide for the controllable modification of the pH of a water source. It would be additionally desirable that such newly developed compositions and methods have associated therewith safety issues and environmental impacts that are no greater than and preferably less than those associated with previous methods of modifying the pH of a water source. It would be desirable to have a new composition that has a minimum of components yet is capable of being formed into a tablet, granule or prill that is strong enough to resist breakage or disintegration during handling, such as transport or packaging, which includes a high percentage of alkali metal hydrogen sulfate, and/or which dissolves at an acceptable rate in aqueous solution.

SUMMARY OF THE INVENTION

In some examples, a composition is provided comprising: (a) about 95 to about 99.999 weight percent of at least one alkali metal hydrogen sulfate; and (b) about 0.001 to less than 0.08 weight percent of at least one alkali metal salt of a fatty carboxylic acid and/or at least one alkaline earth metal salt of a fatty carboxylic acid on a basis of total weight of the composition; wherein the composition comprises less than 1 weight percent of chlorite and/or hypochlorite on a basis of total weight of the composition and less than 1 weight percent on a basis of total weight of the composition of alkali metal salt and/or alkaline earth metal salt that is chemically different from the at least one alkali metal hydrogen sulfate, the at least one alkali metal salt of a fatty carboxylic acid and the at least one alkaline earth metal salt of a fatty carboxylic acid. Also, tablets, prills and granules prepared from the composition are provided.

In some examples, an acidification tablet for acidifying aqueous solutions is provided consisting of at least one alkali metal hydrogen sulfate.

Methods of forming a treated aqueous stream comprising contacting a feed aqueous stream with the composition, tablets, prills and/or granules of the present invention, and a treated water source that has been prepared in accordance with one or more methods of the present invention also are provided.

Methods of forming a treated sanitizing aqueous stream comprising: contacting a first feed aqueous stream with the composition, tablets, prills and/or granules of the present invention, thereby forming a first treated aqueous stream; and combining at least a portion of the first treated aqueous stream with a feed sanitizing aqueous stream comprising free available halogen, thereby forming the treated sanitizing aqueous stream comprising free available halogen, also are provided.

Methods of sanitizing a surface comprising: contacting a first feed aqueous stream with the composition, tablets, prills and/or granules of the present invention, thereby forming a first treated aqueous stream; combining at least a portion of the first treated aqueous stream with a feed sanitizing aqueous stream comprising free available halogen, thereby forming a treated sanitizing aqueous stream comprising free available halogen; and (d) applying the treated sanitizing aqueous stream to a surface to be sanitized.

BRIEF DESCRIPTION OF THE DRAWINGS

In FIGS. 1 through 3, which are not to scale, like reference characters designate the same components and structural features.

DETAILED DESCRIPTION OF THE INVENTION

Figure 1:
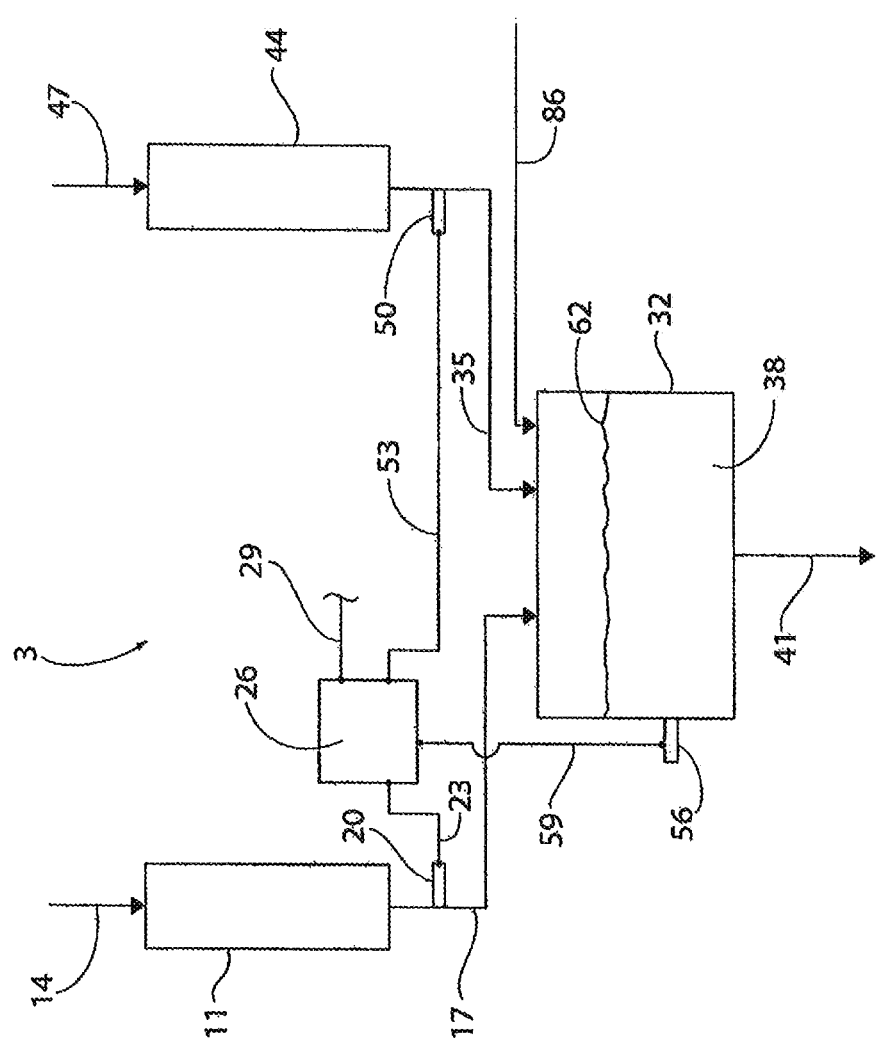
FIG. 1 is a schematic representation of a water treatment system that can be used with a method according to the present invention.

As used herein, spatial or directional terms, such as "left", "right", "inner", "outer", "above", "below", and the like, relate to the invention as it is shown in the drawing figures. However, it is to be understood that the invention can assume various alternative orientations and, accordingly, such terms are not to be considered as limiting.

Other than in the operating examples, or where otherwise indicated, all numbers expressing quantities of ingredients, reaction conditions, processing parameters, physical characteristics, dimensions, and the like used in the specification and claims are to be under stood as modified in all instances by the term "about."

Unless otherwise indicated, all ranges or ratios disclosed herein are to be understood to encompass any and all subranges or subratios subsumed therein. For purposes of non-limiting illustration, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 3.3, 4.7 to 7.5, 5.5 to 10, and the like.

As used herein, the articles "a," "an," and "the" include plural referents unless otherwise expressly and unequivocally limited to one referent.

All documents, such as but not limited to issued patents and patent applications, referred to herein, and unless otherwise indicated, are to be considered to be "incorporated by reference" in their entirety.

The compositions of the present invention can be used to prepare a tablet, granule or prill, e.g., a three-dimensionally shaped object that is composed of the composition of the present invention and which is self-supporting.

The composition of the present invention, in accordance in some examples, is referred to herein as a "tablet composition" or a "tablet(s)."

The compositions of the present invention comprise at least one alkali metal hydrogen sulfate, which in some examples can be in anhydrous form. As used herein, the terms "alkali metal hydrogen sulfate," "alkali metal hydrogen sulfate," "alkali metal bisulfate," "alkali metal bisulfate" and "alkali metal acid sulfate" are equivalent terms.

The alkali metal hydrogen sulfate can be in any suitable form. In some examples, the alkali metal hydrogen sulfate is in the form of a solid particulate material. In some examples, the alkali metal hydrogen sulfate is in the form of a solid particulate material having an average particle size of from 25 microns to 1000 microns, or 50 microns to 1000 microns, or 100 microns to 1000 microns, or 150 microns to 1000 microns, or 200 microns to 1000 microns, or from 250 microns to 800 microns, or from 300 microns to 700 microns, or from 400 microns to 600 microns.

In some examples, the alkali metal hydrogen sulfate material is in prilled form, such as prilled sodium bisulfate which is available from Jones-Hamilton Co. In some examples, the alkali metal hydrogen sulfate can have a particle size distribution of about 10 to about 75, or about 42, weight percent on US standard screen 20 mesh, about 27 to about 76, or about 52, weight percent on 40 mesh, and 0 to about 20, or 5.3, weight percent on 60 mesh, 0 to about 1.9, or about 0.4, weight on 100 mesh, and 0 to about 0.7, or about 0.2, weight percent thru 100 mesh on pan.

The alkali metal of the alkali metal hydrogen sulfate is, in some examples, selected from any suitable alkali metal, such as, but not limited to, lithium, sodium, and potassium. In some examples, the alkali metal of the alkali metal hydrogen sulfate anhydrous is selected from sodium and potassium. The alkali metal hydrogen sulfate is, in some examples, selected from sodium hydrogen sulfate, potassium hydrogen sulfate, and combinations thereof. In some examples, the alkali metal hydrogen sulfate comprises or consists of sodium hydrogen sulfate and/or sodium hydrogen sulfate anhydrous, or consists of sodium hydrogen sulfate anhydrous (sodium bisulfate).

The alkali metal hydrogen sulfate anhydrous, in some examples, contains water in an amount of 0 percent by weight to 1 percent by weight, or from 0 percent by weight to 0.5 percent by weight, or from 0 percent by weight to 0.2 percent by weight, or from 0 percent by weight to 0.1 percent by weight, the percent weights being based on the weight of the alkali metal hydrogen sulfate anhydrous.

In some examples, the alkali metal hydrogen sulfate is present in the composition in an amount of about 95 percent by weight to about 99.999 percent by weight, or about 97 percent by weight to about 99.999 percent by weight, or about 99 percent by weight to 99.999 percent by weight, or about 99.5 percent by weight to about 99.999 percent by weight, or about 99.96 percent by weight to about 99.99 percent by weight, or about 99.98 percent by weight to about 99.99 percent by weight, the percent weights being based on total weight of the composition.

In some examples, an acidification tablet for acidifying an aqueous solution is provided consisting of at least one alkali metal hydrogen sulfate. The one or more alkali metal hydrogen sulfates are present in the acidification tablet in an amount of 100 percent by weight based on total weight of the composition, i.e., the tablet consists of one or more alkali metal hydrogen sulfates and does not include any other components.

In some examples, the composition comprises about 0.001 to less than 0.08 weight percent of at least one alkali metal salt of a fatty carboxylic acid and/or at least one alkaline earth metal salt of a fatty carboxylic acid on a basis of total weight of the composition.

The alkali metal of each alkali metal salt of a fatty carboxylic acid (b) of the compositions of the present invention is, in some examples, independently selected from lithium, sodium and potassium. The alkali metal of each alkali metal salt (b) of the compositions of the present invention is, in some examples, independently selected from sodium and potassium.

The alkaline earth metal of each alkaline earth metal salt of a fatty carboxylic acid (b) of the compositions of the present invention is, in some examples, independently selected from magnesium, calcium and barium. The alkaline earth metal of each alkali metal salt (b) of the compositions of the present invention is, in some examples, independently selected from magnesium and calcium.

The at least one alkali metal salt of a fatty carboxylic acid and/or the at least one alkaline earth metal salt of a fatty carboxylic acid is prepared from a fatty carboxylic acid having from 12 to 20 carbon atoms. In some examples, the at least one alkali metal salt of a fatty carboxylic acid and/or the at least one alkaline earth metal salt of a fatty carboxylic acid is prepared from a fatty carboxylic acid selected from the group consisting of lauric acid (dodecanoic acid), tridecylic acid (tridecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), nonadecylic acid (nonadecanoic acid), arachidic acid (eicosanoic acid) and mixtures thereof.

In some examples, the at least one alkaline earth metal salt of a fatty carboxylic acid is magnesium stearate and/or calcium stearate, or consists of magnesium stearate.

In accordance in some examples, the at least one alkali metal salt of a fatty carboxylic acid and/or the at least one alkaline earth metal salt of a fatty carboxylic acid (b) of the compositions of the present invention is present in an amount of about 0.001 percent by weight to less than 0.08 percent by weight, or about 0.001 percent by weight to about 0.07 percent by weight, or about 0.001 percent by weight to about 0.06 percent by weight, or about 0.001 percent by weight to about 0.04 percent by weight, or about 0.01 percent by weight to about 0.04 percent by weight, or about 0.02 percent by weight to about 0.04 percent by weight, the percent weights being based on total weight of said composition.

The compositions of the present invention can further comprise, in some examples, one or more colorants. Each colorant can, in some examples, be independently selected from one or more dyes, one or more pigments, and combinations thereof. Examples of dyes from which the colorant can be selected, in some examples, include, but are not limited to, dyes having the following US Food and Drug Administration designations: FD&C Blue No. 1, FD&C Blue No. 2, FD&C Green No. 3, FD&C Red No. 40, FD&C Red No. 3, FD&C Yellow No. 5, FD&C Yellow No. 6, and combinations of two or more thereof. Examples of pigments from which the colorant can be selected, in some examples, include, but are not limited to, inorganic pigments, organic pigments, and combinations thereof. Examples of inorganic pigments include, but are not limited to, carbon blacks, and transition metal oxides, such as, titanium dioxide and iron oxides, such as red iron oxide, black iron oxide, and yellow iron oxide. Examples of organic pigments include, but are not limited to: quinacridones; phthalocyanines, such as phthalo green and phthalo blue; naphthols, such as naphthol red; and anthracenes, such as anthacene-9,10-diones, including for example pigments derived from carminic acid, such as carmine. In some examples, the colorant includes carmine. In some examples, the colorant is carmine.

In some examples, the colorant is a food grade colorant, which has been approved by a government body, such as the US Food and Drug Administration for use in foods. Examples of food grade colorants include, but are not limited to, FD&C Blue No. 1, FD&C Blue No. 2, FD&C Green No. 3, FD&C Red No. 40, FD&C Red No. 3, FD&C Yellow No. 5, FD&C Yellow No. 6, and combinations of two or more thereof.

The colorant, in some examples, is present in any suitable amount that provides a desired color to the composition and tablet. The colorant is present, in some examples, for purposes of providing the composition and tablet with a color that allows it to be visually distinguishable from other compositions and tablets, such as other water treatment compositions and tablets, such as calcium hypochlorite compositions and calcium hypochlorite tablets, 1,3,5-trichloro-1,3,5-triazine-2,4,6-trione (also known as trichloro-s-triazinetrione) compositions and tablets, and bromochlorodimethylhydantoin compositions and tablets.

In some examples, the colorant is present in an amount of less than or equal to 10 percent by weight (or up to 10 percent by weight), or less than or equal to 5 percent by weight (or up to 5 percent by weight), or less than or equal to 1 percent by weight (or up to 1 percent by weight) based on the total weight of the composition. In accordance with some further embodiments, the colorant is present in an amount of 0.01 percent by weight to 10 percent by weight, or 0.01 percent by weight to 5 percent by weight, or 0.01 percent by weight to 1 percent by weight, or from 0.02 percent by weight to 0.5 percent by weight, or from 0.03 percent by weight to 0.3 percent by weight, based on the total weight of the composition. In accordance with some additional embodiments, the colorant is present in an amount less than or equal to 0.075 percent by weight (or up to 0.075 percent by weight) such as from 0.01 percent by weight to 0.075 percent by weight, based on the total weight of the composition.

The composition comprises less than 1 weight percent of chlorite and/or hypochlorite on a basis of total weight of the composition, and in some examples is free of chlorite and/or hypochlorite. In some examples, the composition comprises less than 1 weight percent of halide- or chlorine-containing compounds, and in some examples is free of halide- or chlorine-containing compounds.

The composition comprises less than 1 weight percent on a basis of total weight of the composition, or is free of alkali metal salt(s) and/or alkaline earth metal salt(s) that are chemically different from the at least one alkali metal hydrogen sulfate, the at least one alkali metal salt of a fatty carboxylic acid and the at least one alkaline earth metal salt of a fatty carboxylic acid, such as alkali metal halides (for example sodium chloride and/or potassium chloride), alkali metal sulfates (for example sodium sulfate and/or potassium sulfate), and alkaline earth metal sulfates (for example magnesium sulfate, calcium sulfate, and/or barium sulfate).

In some examples of the compositions of the present invention, the alkali metal hydrogen sulfate anhydrous (a) is sodium hydrogen sulfate anhydrous, and the salt (b) is magnesium stearate.

The compositions of the present invention are, in accordance in some examples, free of one or more polysaccharide binders, one or more polyvinylpyrrolidone binders, one or more polyvinyl acetate binders, and one or more polyalkylene glycol ether binders. Examples of polysaccharide binders include, but are not limited to, methyl cellulose binders, hydroxyl propyl cellulose binders, starch binders, sodium alginate binders, and xantham binders. Examples of polyalkylene glycol ether binders include, but are not limited to, polyethylene glycol ether binders, polypropylene glycol ether binders, and poly(ethylene glycol ether propylene glycol ether) binders.

By free of one or more polysaccharide binders, one or more polyvinylpyrrolidone binders, one or more polyvinyl acetate binders, and one or more polyalkylene glycol ether binder, means, in some examples, that the compositions of the present invention contain less than 0.1 percent by weight, or less than 0.05 percent by weight, or less than 0.01 percent by weight, or 0 percent by weight of one or more such materials, based on total weight of the composition.

In some examples, the tablets of the present invention have any desirable shape and dimension. The tablets of the present invention can have, in some examples, a disk-like shape with: a height of from 15 to 50 mm, or from 20 to 40 mm, or from 22 to 35 mm, such as 28 mm; and a diameter of from 3 to 10 cm, or from 4 to 8 cm, or from 5 to 7 cm, such as 6.7 cm.

The tablets of the present invention, in some examples, can have a density of from 1.8 to 2.2 g/cm$^3$, or from 1.80 to 2.20 g/cm$^3$, or from 2.0 to 2.1 g/cm$^3$, or from 2.00 to 2.10 g/cm$^3$, or from 2.01 to 2.08 g/cm$^3$, or from 2.02 to 2.05 g/cm$^3$.

The tablets of the present invention can have, in some examples, a moisture absorption of less than 10 percent by weight, such as from 1 to 10 percent by weight, or from 2 to 9 percent by weight, or from 5 to 8.5 percent by weight, based on the initial weight of the tablet (such as prior to exposure to moisture). The moisture absorption can be determined by suspending a tablet at room temperature (such as 25° C.) above water in a closed container for 200 hours. The tablet is weighed periodically, such as daily, during the course of the test, and the weight of the tablet is compared to that of the tablet prior to being placed in the container, and the percent weight of water absorption is calculated from such comparison. In some examples, the tablets of the present invention have a moisture absorption of from 5 to 8.5 percent by weight, such as 8.1 percent by weight, and are substantially free of crumbling, as determined by subjecting the tablet to torsional and flexural stresses by human hands.

The tablets of the present invention can be formed, in some examples, by mixing (such as dry mixing) together the components thereof, such as the alkali metal hydrogen sulfate (a), salt (b), and optional colorant (c), to form a substantially homogenous composition. The components can be mixed, for example, in a conventional ribbon mixer. The time period for mixing can, for example, range from about 10 minutes to about one hour, or about 15 minutes. The substantially homogenous composition is, in some examples, placed in a mold, such as a metal mold, for example a stainless steel mold, and subjected to elevated pressure for a period of time. The elevated pressure can, in some examples, be at least 10,000 pounds per square inch (psi), such as from 10,000 to 30,000 psi, or from 15,000 to 25,000 psi, such as, 22,000 psi. The tablet mold is opened, and the tablet according to the present invention is removed therefrom. Alternatively, the composition can be formed into prills or granules.

It was found that exposure to ambient conditions or heat helps form a compressed solid with a hardness that allows normal shipping and handling without excessive fragmentation of the tablets, as well as desired dissolution rates to effectively remove residual chlorine from disinfected water. For instance, compressed solids with an average height of 22 mm or 2.2 cm, an average diameter of 2⅝ inches, an average weight of 160 grams, and an average density of 2 can have a hardness (i.e., the ability of a compressed solid to withstand a particular force without breaking in half across the diameter) to withstand a force of 70 to 130 lbf (pound-force), or 80 to 120 lbf, or 90 to 110 lbf, without breaking in half across the diameter. The hardness is determined by applying different amounts of force from a Mecmesin force stand until the compressed solid breaks in half across the diameter.

Compressed solids having the dimensions and parameters previously described can also exhibit a dissolution rate of 1 to 5 pounds per hour (453.6 to 2200 grams per hour) at 68° F., when added to an Acid-Rite™ AR-2500 feeder commercially available from Axiall Corporation of Atlanta, Ga. with a flow rate of 5 gallons per minute of water. The dissolution rate is determined by weighing the tablet before adding it to the feeder, placing the tablet in the feeder, applying water with a flow rate of 5 gallons per minute at 68° F., removing the tablet after a predetermined amount of time, re-weighing the tablet, and then calculating the dissolution rate of the tablet based on the difference in weight per time period water was applied in the feeder.

In accordance with the present invention there is also provided a method of forming a treated aqueous stream, which involves contacting a feed aqueous stream with the composition, tablets, granules or prills of the present invention, as described previously herein. The treated aqueous stream can be formed as a batch process or as a continuous process.

The feed aqueous stream includes, in some examples, water. In some examples, the feed aqueous stream is drawn from an untreated fresh water source, such as untreated well water, untreated river water, untreated lake water, untreated cistern water, and combinations thereof. The feed aqueous stream, with some further embodiments, is drawn from a treated, such as sanitized, fresh water source, such as treated well water, treated river water, treated lake water, treated cistern water, and city water.

In accordance in some examples of the method of the present invention, the treated aqueous stream has a pH that is lower than (or less than) the pH of the feed aqueous stream. In accordance with some further embodiments, the treated aqueous stream has a pH of less than or equal to 8, such as less than or equal to 7.5, such as less than or equal to 7, or from 1 to 8, or from 1 to 7.5, or from 2 to 7, or from 3 to 6.5, or from 4 to 6. In some examples, the treated aqueous stream has a pH of from 6 to 8, or from 6 to 7.5, or from 6 to 7.

The feed aqueous stream can be contacted with the composition of the present invention in any suitable manner. In some examples, the composition of the present invention is contained in a container and the feed aqueous stream is introduced into the container. The introduced feed aqueous stream is, with some batch embodiments, held in the container for a period of time, and then at least a portion thereof removed from the container as the treated aqueous stream. The feed aqueous stream is, with some continuous embodiments, introduced continuously into the container, and the treated aqueous stream is removed continuously from the container.

For purposes of non-limiting illustration and with reference to FIG. 1, the water treatment system 3 includes a first feeder unit 11 that contains the composition, tablets, prills or granules of the present invention (not visible in FIG. 1). A feed aqueous stream is introduced into the first feeder unit 11 as indicated by arrow 14, which also represents a conduit 14. The feed aqueous stream and the composition, tablets, prills or granules of the present invention are contacted together within first feeder unit 11. A treated aqueous stream is withdrawn from first feeder unit 11 as indicated by arrow 17, which also represents a conduit 17. The pH of the treated aqueous stream passing through conduit 17 is measured by a suitable probe, such as probe 20. The pH output signals of probe 20 are relayed to a processor unit 26 by electrical connection 23. Processor unit 26 can be connected to an external power source, not shown, by electrical connection 29. Depending on the pH values transmitted to processor unit 26, the amount and rate of feed aqueous stream introduced into first feeder unit 11 and/or the amount and rate of treated aqueous stream removed from first feed unit 11 can be adjusted by one or more valves, such as remotely controlled valves, not shown. The treated aqueous stream passing through conduit 17 can be used for any suitable purpose, such as but not limited to: application to a surface, such as equipment surfaces and/or food surfaces, for purposes of cleaning the surface; and/or combination with another aqueous stream for purposes adjusting the pH of the other aqueous stream.

In accordance with the present invention there is further provided a method of forming a treated sanitizing aqueous stream, that involves forming a first treated aqueous stream, such as the treated aqueous stream as described above, and combining at least a portion of the first treated aqueous stream with a feed sanitizing stream that includes free available halogen, thereby forming the treated sanitizing aqueous stream that includes free available halogen.

The first treated aqueous stream and the feed sanitizing stream can be combined by any suitable method or methods. In some examples, the first treated aqueous stream and the feed sanitizing stream are combined together in a mixing tank, such as in accordance with the non-limiting embodiments as described further herein with reference to FIG. 1. The first treated aqueous stream and the feed sanitizing stream are combined together, in some examples, by introducing the first treated aqueous stream into a conduit carrying the feed sanitizing aqueous stream, such as in accordance with the non-limiting embodiments as described further herein with reference to FIG. 2. The first treated aqueous stream and the feed sanitizing aqueous stream are combined together, with some further embodiments, by introducing the feed sanitizing aqueous stream into a conduit carrying the first treated aqueous stream, not depicted in the drawings. The first treated aqueous stream and the feed sanitizing stream are combined together, with some additional embodiments, by introducing the first treated aqueous stream and the feed sanitizing aqueous stream into a conduit carrying a primary aqueous stream, such as in accordance with the non-limiting embodiments as described further herein with reference to FIG. 3.

The term "free available halogen" as used herein means halogen that is present in an oxidized form in an aqueous solution, such as the feed sanitizing stream and the treated sanitizing aqueous stream. Free available halogen (FAH) is present in the form of hypohalous acid (HOX) and/or hypohalite anion (XO$^-$), wherein X represents a halogen group having a +1 oxidation state. The halogen, X, of the free available halogen is selected from chlorine, bromine and iodine, in some examples.

The free available halogen of the feed sanitizing aqueous stream and the treated sanitizing aqueous stream, in some examples, includes free available chlorine, free available bromine, or free available iodine. In some examples, the free available halogen of the feed sanitizing aqueous stream and the treated sanitizing aqueous stream includes, or is, free available chlorine.

The amount of free available halogen present in the feed sanitizing aqueous stream and the treated sanitizing aqueous stream can vary, provided that, in some examples, the treated sanitizing aqueous stream includes at least a sufficient amount of free available halogen such that it can be used to clean and/or sanitize one or more surfaces to which it is applied. In some examples, the amount of free available halogen in the treated sanitizing aqueous stream is less than the amount of free available halogen present in the feed sanitizing aqueous stream, because the treated aqueous stream is combined with the feed sanitizing aqueous stream, thereby resulting in a reduced or diluted amount of free available halogen within the resulting treated sanitizing aqueous stream.

In some examples, the amount of free available halogen present in the treated sanitizing aqueous stream is from 0.001 percent to 99.9 percent less than, or from 10 percent to 90 percent less than, or from 25 percent to 75 percent less than the amount of free available halogen present in the feed sanitizing aqueous stream.

The amount of free available halogen present in the treated sanitizing aqueous stream and the amount of free available halogen present in the feed sanitizing aqueous stream are, in some examples, each independently from 10 ppm to 100,000 ppm, or from 30 ppm to 30,000 ppm, or from 50 to 20,000 ppm, or from 50 ppm to 5000 ppm, or from 50 ppm to 1000 ppm, or from 50 ppm to 500 ppm provided that, with some further embodiments, the amount of free available halogen present in the treated sanitizing aqueous stream is lower than the amount of free available halogen present in the feed sanitizing aqueous stream. With some further embodiments, the amount of free available halogen present in the treated sanitizing aqueous stream is at least 1 ppm, such as from 1 ppm to 1000 ppm, or from 1 ppm to 500 ppm, or from 30 ppm to 50 ppm.

The free available halogen of the treated sanitizing aqueous stream includes, in some examples, free available chlorine, and the treated sanitizing aqueous stream has a pH of 6 to 8, or 6 to 7.5, or 6 to 7.

The feed sanitizing aqueous stream, in accordance in some examples, is formed by contacting a second feed aqueous stream with a source of free available halogen. The source of free available halogen releases free available halogen into the second feed aqueous stream, thereby resulting in formation of the feed sanitizing aqueous stream.

The source of free available halogen, in some examples, is selected from calcium hypochlorite, sodium hypochlorite, potassium hypochlorite, lithium hypochlorite, chlorine gas, 1,3,5-trichloro-1,3,5-triazine-2,4,6-trione, 1-bromo-3-chloro-5,5-dimethylhydantoin, and combinations thereof.

The first and second feed aqueous streams each independently include water, in some examples. With some further embodiments, the first and second feed aqueous streams are each independently drawn from an untreated fresh water source, such as untreated well water, untreated river water, untreated lake water, untreated cistern water, and combinations thereof. The first and second feed aqueous streams, with some additional embodiments, are each independently drawn from a treated, such as sanitized, fresh water source, such as treated well water, treated river water, treated lake water, treated cistern water, and city water. The first and second feed aqueous streams are, in some examples, drawn from the same or different sources. The first and second feed aqueous streams are the same or different, in some examples.

In accordance in some examples of the present invention, for purposes of non-limiting illustration, and with reference to the water treatment system 3 of FIG. 1, one or more tablets according to the present invention are contained within first feeder unit 11. A first feed aqueous stream is introduced into first feeder unit 11 as indicated by arrow 14, which also represents a conduit 14. The first feed aqueous stream and the composition, tablets, prills or granules according to the present invention are contacted with each other within first feeder unit 11. A first treated aqueous stream is formed in and withdrawn from first feeder unit 11 as indicated by arrow 17, which also represents a conduit 17.

The first treated aqueous stream is forwarded through conduit 17 and into mixing tank 32 where it is combined with a feed sanitizing aqueous stream that has been forwarded through conduit 35 into mixing tank 32. Mixing tank 32 can include one or more dynamic mixers, such as one or more impellers, not shown. A treated sanitizing aqueous stream 38 is accordingly formed within mixing tank 32. The treated sanitizing aqueous stream 38 is removed and forwarded from mixing tank 32 through conduit 41. The treated sanitizing aqueous stream 38 can be held within mixing tank 32 and intermittently released from mixing tank 38 through conduit 41. Alternatively, the treated sanitizing aqueous stream 38 can be continuously removed from mixing tank 32 and continuously forwarded through conduit 41 as the sanitizing aqueous stream 38 is formed within mixing tank 32.

With further reference to FIG. 1, the feed sanitizing aqueous stream is formed within second feeder unit 44. Second feeder unit 44 includes a source of free available halogen, such as calcium hypochlorite, which can be in form of one or more calcium hypochlorite tablets. A second feed aqueous stream is introduced into second feeder unit 44 as indicated by arrow 47, which also represents a conduit 47. The second feed aqueous stream contacts the source of free available halogen within second feeder unit 44, which results in formation of the feed sanitizing aqueous stream that is removed from second feeder unit 44 and forwarded to mixing tank 32 through conduit 35.

The pH of the first treated aqueous stream can be measured as it passes through conduit 17 by probe 20 as described previously herein with regard to the treated aqueous stream. The pH and/or conductivity of the feed sanitizing aqueous stream passing through conduit 35 can be measured by probe 50. The pH and/or conductivity data measured by probe 50 are forwarded to processor unit 26 by electrical connection 53. Depending on the pH and/or conductivity values transmitted to processor unit 26 through electrical connection 53, the amount and rate of the second feed aqueous stream introduced into second feeder unit 44 through conduit 47 and/or the amount and rate of the feed sanitizing aqueous stream removed from second feed unit 44 through conduit 35 can be adjusted by one or more valves, such as remotely controlled valves, not shown.

The pH of the treated sanitizing aqueous stream 38 formed within mixing tank 32 can be measured by probe 56. Alternatively, or additionally, probe 56 can be placed in contact with conduit 41 so as to measure the pH of the treated sanitizing aqueous stream passing therethrough (not depicted in FIG. 1). The pH values measured by probe 56 are transmitted to processor unit 26 by electrical connection 59. Depending on the pH values transmitted to processor unit 26 through electrical connection 59, the amount and rate of the treated aqueous stream introduced into mixing tank 32 through conduit 17 and/or the amount and rate of the feed sanitizing aqueous stream introduced into mixing tank 32 through conduit 35 can be adjusted by one or more valves, such as remotely controlled valves, not shown.

In some examples, the level 62 of treated sanitizing aqueous stream 38 within mixing tank 32 can be measured by one or more probes (not shown) and transmitted to processor unit 26. The level 62 can be adjusted by adjusting the amount and rate of the treated aqueous stream introduced into mixing tank 32 through conduit 17, and/or adjusting the amount and rate of the feed sanitizing aqueous stream introduced into mixing tank 32 through conduit 35, and/or adjusting the amount and rate of treated sanitizing aqueous stream removed from mixing tank 32 through conduit 41 by one or more valves, such as remotely controlled valves, not shown.

In accordance in some examples, a third feed aqueous stream can be introduced and mixed or combined with the treated aqueous stream and the feed sanitizing aqueous stream. The third feed aqueous stream can be introduced for purposes including, but not limited to, adjusting the concentration of free available halogen present in the resulting treated sanitizing aqueous stream (such as by dilution). The third feed aqueous stream can be selected from one or more of those sources as described previously herein with regard to the first and second feed aqueous streams, such as city water.

For purposes of non-limiting illustration, attention is directed to treatment system 3 of FIG. 1, in which a third feed aqueous stream is introduced into mixing tank 32 as indicated by arrow 86, which also represents a conduit 86, in some examples of the present invention. The rate and flow of the third feed aqueous stream introduced into mixing tank 32 can be controlled by one or more valves (not shown), which may be controlled by processor unit 26 in response to signals transmitted thereto by one or more probes in probing contact with conduit 86 (not shown).

Figure 2:
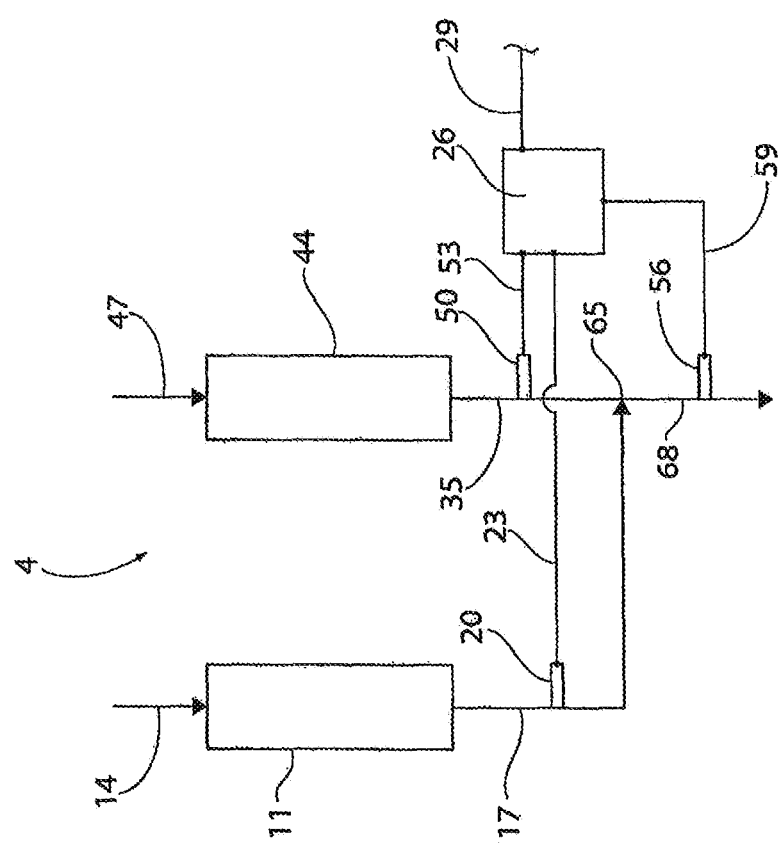
FIG. 2 is a schematic representation of another water treatment system that can be used with a method according to the present invention.

The method of forming a treated sanitizing aqueous stream in some examples of the present invention can be performed with the water treatment system 4 of FIG. 2. For purposes of non-limiting illustration and with reference to FIG. 2, a first treated aqueous stream is formed in first feeder unit 11 and forwarded through conduit 17 as described previously herein. A feed sanitizing aqueous stream is formed in second feeder unit 44 and forwarded through conduit 35 as described previously herein. Conduit 17 is in fluid communication with conduit 35 at intersection point 65. At intersection point 65 the first treated aqueous stream forwarded through conduit 17 is combined with the feed sanitizing aqueous stream forwarded through conduit 35, which results in the formation of a treated sanitizing aqueous stream that is forwarded from intersection point 65 through conduit 68.

The pH of the treated sanitizing aqueous stream forwarded through conduit 68 is measured by probe 56 in accordance with the description provided previously herein with regard to measurement of the pH of the treated sanitizing aqueous stream within mixing tank 32 of water treatment system 3 of FIG. 1.

In accordance in some examples of the present invention, the method of forming a treated sanitizing aqueous stream includes: providing a primary aqueous stream; forming a first treated aqueous stream, as described previously herein; combining the first treated aqueous stream with the primary aqueous stream; and combining a feed sanitizing aqueous stream with the primary aqueous stream, upstream and/or downstream of where the first treated aqueous stream is combined with the primary aqueous stream, thereby forming the treated sanitizing aqueous stream. With some further embodiments, the first treated aqueous stream is combined with the primary aqueous stream upstream and/or downstream of where the feed sanitizing aqueous stream is combined with the primary aqueous stream. The feed sanitizing aqueous stream can be formed, in some examples, in accordance with the description provided previously herein.

In some examples, the method of forming a treated sanitizing aqueous stream includes: providing a primary aqueous stream; forming a first treated aqueous stream, as described previously herein; combining the first treated aqueous stream with the primary aqueous stream, thereby forming an intermediate primary aqueous stream; and combining a feed sanitizing aqueous stream with the intermediate primary aqueous stream, downstream of where the first treated aqueous stream is combined with the primary aqueous stream, thereby forming the treated sanitizing aqueous stream.

With some further embodiments, the method of forming a treated sanitizing aqueous stream includes: providing a primary aqueous stream; combining a feed sanitizing aqueous stream with the primary aqueous stream, thereby forming an intermediate primary aqueous stream; forming a first treated aqueous stream, as described previously herein; and combining the first treated aqueous stream with the intermediate primary aqueous stream, downstream of where the feed sanitizing aqueous stream is combined with the primary aqueous stream, thereby forming the treated sanitizing aqueous stream.

The primary aqueous stream can, in some examples, be selected from those sources as described previously herein with regard to the first and second feed aqueous streams, such as (but not limited to) city water.

Figure 3:
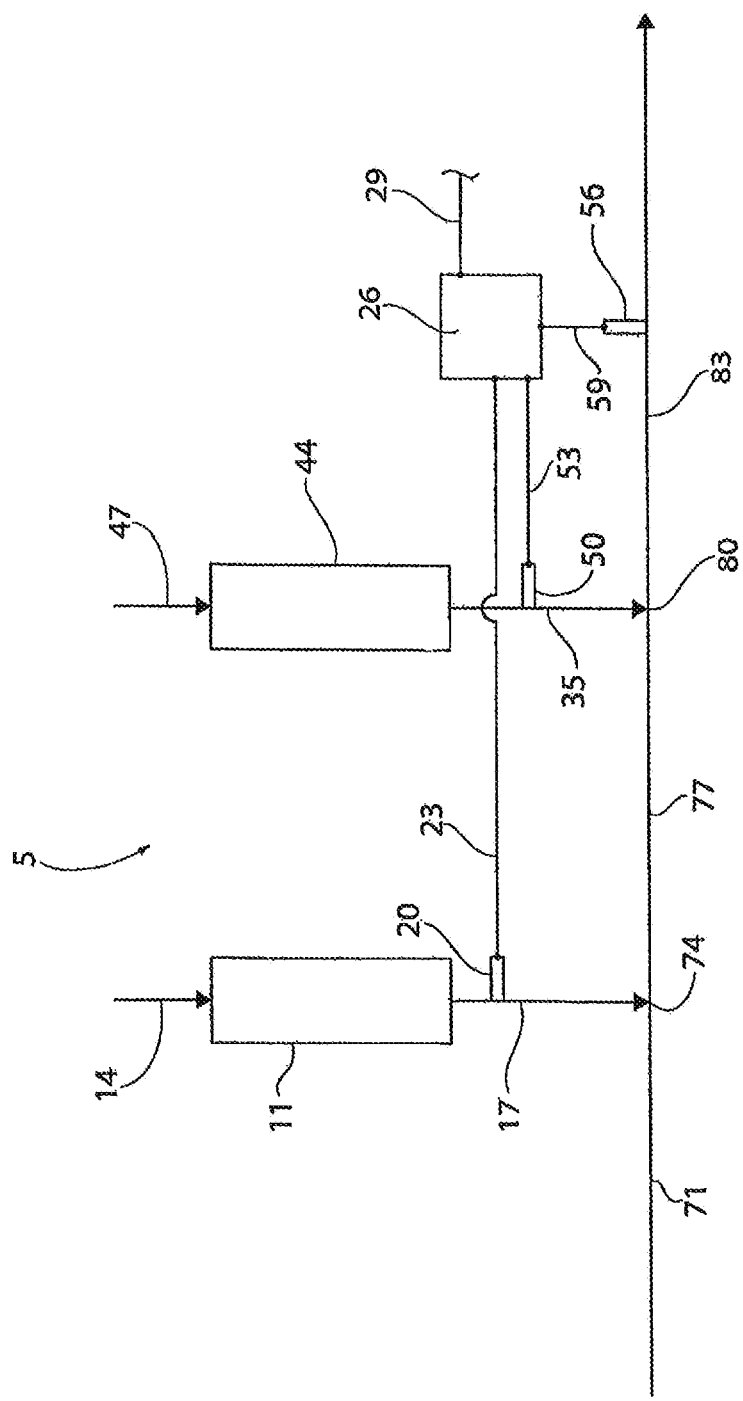
FIG. 3 is a schematic representation of a further water treatment system that can be used with a method according to the present invention.

For purposes of non-limiting illustration and with reference to the water treatment system 5 of FIG. 3, a primary aqueous stream is provided from a source (not shown) and forwarded through conduit 71 (or conduit segment 71). A treated aqueous stream is formed in feeder unit 11, as described previously herein, and combined with the primary aqueous stream at intersection point or junction 74 with conduit 71. The primary aqueous stream with the treated aqueous stream combined therewith (which can be referred to as an intermediate primary aqueous stream in some examples) is forwarded through conduit 77 (or conduit segment 77).

With further reference to FIG. 3, a feed sanitizing aqueous stream is formed in feeder unit 44 and forwarded through conduit 35 as described previously herein. The feed sanitizing aqueous stream is combined with the intermediate primary aqueous stream at intersection point or junction 80 with conduit (or conduit portion) 77, which results in the formation of a treated sanitizing aqueous stream that is forwarded through conduit (or conduit portion) 83. Intersection point 80 is downstream of intersection point 74, and intersection point 74 is upstream of intersection point 80.

The pH of the first aqueous feed stream forwarded through conduit 17, and the pH and/or conductivity of the feed sanitizing aqueous stream forwarded through conduit 35 can be measured by probes 20 and 50 and transmitted to process controller 26 by electrical connections 23 and 53 as described previously herein with regard to water treatment systems 3 and 4. The pH and/or conductivity of the treated sanitizing aqueous stream forwarded through conduit 83 can be measured with one or more probes, such as represented by probe 56, that are in probing contact with conduit 83, which can relay measurement data to processor controller 26 by electrical connection 59, as described previously herein. The amount and rate of, the primary aqueous stream flowing through conduit 71, the treated aqueous stream flowing through conduit 17, the feed sanitizing aqueous stream flowing through conduit 35, and the treated sanitizing aqueous stream flowing through conduit 83 can each be independently controlled by processor unit 26 by one or more valves (not shown).

With some further alternative embodiments, conduit 35 is in fluid communication with intersection point 74, and conduit 17 is in fluid communication with intersection point 80 (not depicted in FIG. 3), in which case the feed sanitizing aqueous stream is combined with the primary aqueous stream at intersection point 74, which results in the formation of an intermediate primary aqueous stream, which is forwarded through conduit 77. Correspondingly, downstream of where the feed sanitizing aqueous stream is combined with the primary aqueous stream (at intersection point 74), the first treated aqueous stream is combined with the intermediate primary aqueous stream at intersection point 80, which results in formation of the treated sanitizing aqueous stream, which is forwarded through conduit 83.

In accordance with the present invention there is additionally provided a method of treating a surface, such as cleaning and/or sanitizing a surface, that includes forming a treated sanitizing aqueous stream as described previously herein, and then applying the treated sanitizing aqueous stream to a surface to be treated, such as to be cleaned and/or sanitized. The treated sanitizing aqueous stream can be applied by any appropriate method, examples of which include but are not limited to: spray application; wiping with soaked rags; curtain or waterfall application; and soaking by immersion.

The surface, in some examples, to be sanitized, by application of the treated sanitizing aqueous stream thereto, is selected from vegetable surfaces, fruit surfaces, equipment surfaces, animal carcass surfaces, and combinations thereof, in some examples. Additional surfaces that can be sanitized in accordance with the method of the present invention include, but are not limited to: harvested vegetables, such as potatoes, sweet potatoes, tomatoes, rutabagas, beets, and mushrooms; harvested fruits, such as apples, oranges, plums, pears, and mangos; metal surfaces in food processing plants, such as meat procession plants; equipment in breweries, such as fermenting tubs, mash tuns, pipe interiors, and pipe exteriors; fowl carcasses in fowl processing plants, such as chicken carcasses in chicken processing plants, and turkey carcasses in turkey processing plants; beef carcasses in beef processing plants; and pork carcasses in pork processing plants.

The present invention is more particularly described in the examples that follow, which are intended to be illustrative only, since numerous modifications and variations therein will be apparent to those skilled in the art.

Examples

Tablet Compositions and Tablet Preparation

Tablets were formed by mixing the components as specified in Table 1 to form a dry blended composition. As used herein, a "dry blended composition" refers to a substantially homogenous mixture of dry materials. The sodium bisulfate and magnesium stearate, and optionally colorant, were blended in a ribbon mixer for 15 minutes to form a dry blended composition. Fifty pounds total of each composition was prepared. Examples 5-8 are examples according to the present invention. Examples 1-4 are comparative examples.

After mixing, tablets were prepared from each dry blended composition by compaction to form a compressed solid or tablet. Approximately 300 grams of each dry blended composition prepared in Examples 1-8 were placed into a hopper of a Baldwin 20 or 45 tablet press. After adding the respective dry blended composition to the tablet press, pressure was applied to the composition to form well-defined tablets. The resulting tablets were cylindrical in shape, and had a height of 2⅝ inches. The resulting tablets had an average density of 2.

TABLE 1

| Component | Example 1 Wt. % | Example 2 Wt. % | Example 3 Wt. % | Example 4 Wt. % | Example 5 Wt. % | Example 6 Wt. % | Example 7 Wt. % | Example 8 Wt. % |
|---|---|---|---|---|---|---|---|---|
| Sodium Bisulfate (Sodium Acid Sulfate)[1] | 99.36 | 99.68 | 99.84 | 99.92 | 99.96 | 99.98 | 100.00 | 99.95 |
| Magnesium Stearate | 0.64 | 0.32 | 0.16 | 0.08 | 0.04 | 0.02 | 0 | 0.02 |
| Red Colorant[2] | 0 | 0 | 0 | 0 | 0 | 0 | 0 | 0.03 |
| Acceptable Tablet Formation[3] | NO | NO | NO | NO | YES | YES | YES | YES |

[1]Sodium Bisulfate, being prilled (as purchased from Jones-Hamilton Co.), having a particle size distribution typically having 42 (range 10-75) Wt. % on 20 mesh, typically having 52 (range 27-76) Wt. % on 40 mesh, typically having 5.3 (range 0-20) Wt. %, typically having 0.4 (range 0-1.9) Wt. % on mesh 100, and typically having 0.2 (range 0-0.7) Wt. % thru mesh 100 on pan.
[2]Berry Microfine Commercially available from Sensient Colors LLC.
[3]This was determined from analysis of the tablet during ejection from the press (Baldwin 20 &/or 45) and after ejection through analysis of dust, chips, uniformity, and hardness.

Tablets prepared from Tablet Compositions 1-4 did not form a cohesive tablet and fell apart in the hand. Tablets prepared from Tablet Compositions 5-8 were subject to visual and tactile evaluation and determined to have a desirable balance of both hardness and density. It is believed that the tablets of Compositions 5, 6 and 8 provide suitable characteristics for tableting that will reduce the need to interrupt the tableting operation to clean the dies. The tablets of Composition 7 also formed tablets having desirable hardness properties.

The present invention has been described with reference to specific details of particular embodiments thereof. It is not intended that such details be regarded as limitations upon the scope of the invention except insofar as and to the extent that they are included in the accompanying claims.

What is claimed is:

1. A composition comprising:
   (a) about 95 to about 99.999 weight percent of at least one alkali metal hydrogen sulfate in prilled form; and
   (b) about 0.001 to less than 0.08 weight percent of at least one alkali metal salt of a fatty carboxylic acid and/or at least one alkaline earth metal salt of a fatty carboxylic acid on a basis of total weight of the composition;
   wherein the composition comprises less than 0.1 weight percent of chlorite and/or hypochlorite on a basis of total weight of the composition and less than 1 weight percent on a basis of total weight of the composition of alkali metal salt and/or alkaline earth metal salt that is chemically different from the at least one alkali metal hydrogen sulfate, the at least one alkali metal salt of a fatty carboxylic acid and the at least one alkaline earth metal salt of a fatty carboxylic acid.

2. The composition according to claim 1, wherein the at least one alkali metal hydrogen sulfate comprises alkali metal hydrogen sulfate anhydrous.

3. The composition according to claim 1, wherein the at least one alkali metal hydrogen sulfate consists of alkali metal hydrogen sulfate anhydrous.

4. The composition according to claim 2, wherein the alkali metal hydrogen sulfate anhydrous contains water in an amount of about 0 percent by weight to about 1 percent by weight, based upon total weight of the alkali metal hydrogen sulfate anhydrous present in the composition.

5. The composition according to claim 1, wherein the at least one alkali metal hydrogen sulfate is present in an amount of from about 99 percent by weight to about 99.999 percent by weight on a basis of total weight of the composition.

6. The composition according to claim 1, wherein the at least one alkali metal salt of a fatty carboxylic acid comprises an alkali metal selected from the group consisting of lithium, sodium and potassium.

7. The composition according to claim 1, wherein the at least one alkaline earth metal salt of a fatty carboxylic acid comprises an alkaline earth metal selected from the group consisting of magnesium, calcium and barium.

8. The composition according to claim 1, wherein the at least one alkali metal salt of a fatty carboxylic acid and/or the at least one alkaline earth metal salt of a fatty carboxylic acid is prepared from a fatty carboxylic acid having from 6 to 24 carbon atoms.

9. The composition according to claim 1, wherein the at least one alkali metal salt of a fatty carboxylic acid and/or the at least one alkaline earth metal salt of a fatty carboxylic acid is prepared from a fatty carboxylic acid selected from the group consisting of lauric acid (dodecanoic acid), tridecylic acid (tridecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), nonadecylic acid (nonadecanoic acid), arachidic acid (eicosanoic acid) and mixtures thereof.

10. The composition according to claim 1, wherein the at least one alkaline earth metal salt of a fatty carboxylic acid is magnesium stearate and/or calcium stearate.

11. The composition according to claim 1, wherein the at least one alkaline earth metal salt of a fatty carboxylic acid is magnesium stearate.

12. The composition according to claim 1, wherein the at least one alkali metal salt of a fatty carboxylic acid and/or the at least one alkaline earth metal salt of a fatty carboxylic acid (b) is present in an amount of from about 0.001 weight percent to about 0.04 weight percent on a basis of total weight of the composition.

13. The composition according to claim 1, wherein the at least one alkali metal salt of a fatty carboxylic acid and/or the at least one alkaline earth metal salt of a fatty carboxylic acid (b) is present in an amount of from about 0.02 weight percent to about 0.04 weight percent on a basis of total weight of the composition.

14. The composition according to claim 1, wherein the composition is free of chlorite and/or hypochlorite.

15. The composition according to claim 1, wherein the composition is free of alkali metal salt and/or alkaline earth metal salt that is chemically different from the at least one alkali metal hydrogen sulfate, the at least one alkali metal salt of a fatty carboxylic acid and the at least one alkaline earth metal salt of a fatty carboxylic acid.

16. The composition according to claim 1, wherein the composition comprises sodium hydrogen sulfate anhydrous and magnesium stearate, and optionally colorant.

17. The composition according to claim 1, wherein the composition consists of sodium hydrogen sulfate anhydrous, magnesium stearate and colorant.

18. The composition according to claim 1, wherein the composition consists of sodium hydrogen sulfate anhydrous and magnesium stearate.

19. The composition according to claim 1, further comprising a colorant selected from the group consisting of dyes, pigments, and combinations thereof.

20. The composition according to claim 19, wherein the colorant is a food grade colorant and is present in an amount of less than or equal to about 1 percent by weight, based on the total weight of the composition.

21. The composition according to claim 19, wherein the colorant comprises carmine.

22. The composition according to claim 1, wherein the composition is free of one or more polysaccharide binders, one or more polyvinylpyrrolidone binders, one or more polyvinyl acetate binders, and one or more polyalkylene glycol ether binders.

23. A tablet prepared from the composition according to claim 1.

24. The tablet according to claim 23, wherein the tablet has a density of about 1.8 g/cm$^3$ to about 2.2 g/cm$^3$.

25. An acidification tablet for acidifying an aqueous solution comprising the composition according to claim 1.

26. The acidification tablet according to claim 25, wherein the alkali metal hydrogen sulfate is sodium bisulfate.

27. A method of forming a treated aqueous stream comprising:
   (a) contacting a feed aqueous stream with a composition according to claim 1, thereby forming a treated aqueous stream.

28. The method according to claim 27, wherein the treated aqueous stream has a pH that is lower than a pH of the feed aqueous stream.

29. The method according to claim 27, wherein the pH of the treated aqueous stream is less than or equal to 8.

30. A method of forming a treated aqueous stream comprising:
   (a) contacting a feed aqueous stream with a tablet according to claim 25, thereby forming a treated aqueous stream.

31. A method of forming a treated sanitizing aqueous stream comprising:
   (a) contacting a first feed aqueous stream with a composition according to claim 1, thereby forming a first treated aqueous stream; and
   (b) combining at least a portion of the first treated aqueous stream with a feed sanitizing aqueous stream comprising free available halogen, thereby forming a treated sanitizing aqueous stream comprising free available halogen.

32. The method according to claim 31, wherein the treated sanitizing aqueous stream comprises free available chlorine.

33. The method according to claim 31, wherein the treated sanitizing aqueous stream has a pH of about 6 to about 8.

34. The method according to claim 31, wherein the feed sanitizing aqueous stream is formed by contacting a second feed aqueous stream with a source of free available halogen.

35. The method according to claim 31, wherein the source of free available halogen is selected from the group consisting of calcium hypochlorite, sodium hypochlorite, potassium hypochlorite, lithium hypochlorite, chlorine gas, 1,3,5-trichloro-1,3,5-triazine-2,4,6-trione, 1-bromo-3-chloro-5,5-dimethylhydantoin and combinations thereof.

36. A method of sanitizing a surface comprising:
   (a) contacting a first feed aqueous stream with the composition according to claim 1, thereby forming a first treated aqueous stream;
   (b) combining at least a portion of the first treated aqueous stream with a feed sanitizing aqueous stream comprising free available halogen, thereby forming a treated sanitizing aqueous stream comprising free available halogen; and
   (c) applying the treated sanitizing aqueous stream to a surface to be sanitized.

37. The method according to claim 36, wherein the surface to be sanitized is selected from the group consisting of vegetable surfaces, fruit surfaces, equipment surfaces, animal carcass surfaces, and combinations thereof.

* * * * *